US006218505B1

(12) United States Patent
Panzone et al.

(10) Patent No.: US 6,218,505 B1
(45) Date of Patent: Apr. 17, 2001

(54) CHEMICAL PROCESS FOR PREPARING AMIDE DERIVATIVES OF ANTIBIOTIC A 40926

(75) Inventors: Gianbattista Panzone, Cornaredo; Alessandra Maria Marazzi, Saronno; Ermenegildo Restelli, Gerenzano; Anacleto Gianantonio, Milan, all of (IT)

(73) Assignee: Biosearch Italia S.p.A. (IT)

( * ) Notice: Subject to any disclaimer, the term of this patent is extended or adjusted under 35 U.S.C. 154(b) by 0 days.

(21) Appl. No.: 09/155,869

(22) PCT Filed: Apr. 15, 1997

(86) PCT No.: PCT/EP97/01874

§ 371 Date: Oct. 7, 1998

§ 102(e) Date: Oct. 7, 1998

(87) PCT Pub. No.: WO97/40067

PCT Pub. Date: Oct. 30, 1997

(30) Foreign Application Priority Data

Apr. 23, 1996 (GB) .................................................. 96106341

(51) Int. Cl.[7] ............................. C07K 1/113; C07K 1/16; C07K 9/00
(52) U.S. Cl. ........................... 530/322; 530/344; 530/345
(58) Field of Search ...................... 514/8, 9, 11; 530/317, 530/322, 321, 333, 345, 344

(56) References Cited

U.S. PATENT DOCUMENTS

| 4,239,751 | 12/1980 | Coronelli et al. | 424/118 |
| 4,542,018 | 9/1985 | Borghi et al. | 424/119 |

(List continued on next page.)

FOREIGN PATENT DOCUMENTS

| 0 122 969 | 10/1984 | (EP) . |
| 0 177 882 | 4/1986 | (EP) . |

(List continued on next page.)

OTHER PUBLICATIONS

Malabarba et al., New Semisynthetic Glycopeptides . . . J. Antibiotics. vol. 48, No. 8, pp. 869–883, Aug. 1995.*

Omura et al., Chemical Abstracts, vol. 101, No. 7, Aug., 1984, p. 318, Abstract No. 51459t (reprint included).

Pavlov et al., Journal of Antibiotics, Feb. 1996, pp. 194–198, vol. 49, No. 2.

*Primary Examiner*—Jeffrey E. Russel
(74) *Attorney, Agent, or Firm*—Killworth, Gottman, Hagan & Schaeff, L.L.P.

(57) ABSTRACT

Improved chemical process for preparing the compounds of formula (I), wherein: $R_1$ represents $(C_9–C_{12})$alkyl; M represents hydrogen, α-D-mannopyranosyl or 6-O-acetyl-α-D-mannopyranosyl and Y represents an amino group of formula $—NR_2\text{-alk}_1\text{-}(NR_3\text{-alk}_2)_p\text{-}(NR_4\text{-alk}_3)_q\text{-}W$. One aspect of the invention refers to the preparation of the intermediate compound of formula (III) (which corresponds to the above compound of formula (I)

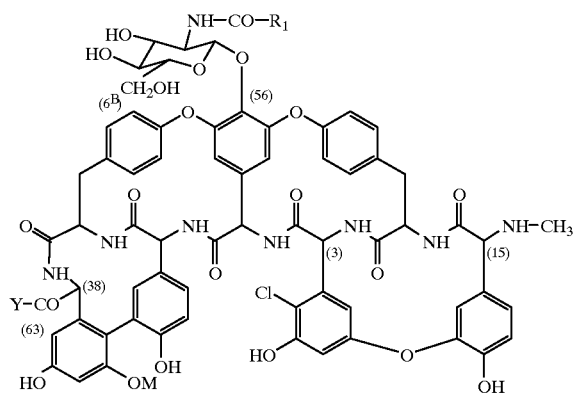

(I)

wherein $R_1$ and M are as above defined and Y is hydroxy), by reacting a compound of formula (II) (which corresponds to the above compound of formula (I) wherein $R_1$ and M are as above defined and Y is hydroxymethyl), with a $(C_1–C_4)$ alkanol in the presence of a concentrated mineral acid, using the same alkanol as the reaction solvent and submitting the obtained ester compound to a reductive process by adding an alkali metal borohndride into the same reaction mixture. A further aspect of the invention refers to the amidation reaction for obtaining the compound of formula (I), which is carried out by reacting a compound of formula (III) with a suitable amine of formula (IV): $NHR_3\text{-alk}_1\text{-}(NR_4\text{-alk}_2)_p\text{-}(NR_5\text{-alk}_3)_q\text{-}W$, wherein $R_3$, $R_4$, $R_5$, $\text{alk}_1$, $\text{alk}_2$, $\text{alk}_3$, p, q and W are as defined in formula (I), in an inert organic solvent, in the presence of a condensing agent and setting the initial pH of the mixture (measured after diluting a sample of the reaction mixture with 9 volumes of water) at a value of from 6.5 to 9.0. By combining the above improved steps into a single process, it is possible to set up a particularly convenient process for preparing the compounds of formula (I). In addition, a purification method involving the use of polyamide resins and aqueous eluents is provided.

30 Claims, No Drawings

U.S. PATENT DOCUMENTS

| | | | |
|---|---|---|---|
| 4,594,187 | 6/1986 | Strazzolini et al. | 530/332 |
| 4,629,781 | 12/1986 | Strazzolini et al. | 530/317 |
| 4,650,855 | 3/1987 | Malabarba et al. | 530/322 |
| 4,698,418 | 10/1987 | Malaberba et al. | 530/317 |
| 4,782,042 | 11/1988 | Selva et al. | 514/9 |
| 4,789,661 | 12/1988 | Malabarba et al. | 514/8 |
| 4,868,171 | 9/1989 | Selva et al. | 514/183 |
| 4,882,419 | 11/1989 | Malabarba et al. | 530/317 |
| 4,914,187 | 4/1990 | Malabarba et al. | 530/317 |
| 4,927,754 | 5/1990 | Assi et al. | 435/71.3 |
| 4,935,238 | 6/1990 | Selva et al. | 424/118 |
| 4,954,483 | 9/1990 | Malabarba et al. | 514/9 |
| 4,994,555 | 2/1991 | Panzone et al. | 530/344 |
| 5,064,811 | 11/1991 | Borghi et al. | 514/8 |
| 5,085,990 | 2/1992 | Lancini et al. | 435/71.3 |
| 5,108,988 | 4/1992 | Ciabatti et al. | 514/11 |
| 5,185,320 | 2/1993 | Trani et al. | 514/8 |
| 5,194,424 | 3/1993 | Malabarba et al. | 514/8 |
| 5,198,418 | 3/1993 | Malabarba et al. | 514/8 |
| 5,438,117 | 8/1995 | Malabarba et al. | 530/317 |
| 5,486,465 | 1/1996 | Giantonio et al. | 435/70.1 |
| 5,491,128 | 2/1996 | Ciabatti et al. | 514/11 |
| 5,500,410 | 3/1996 | Malabarba et al. | 514/8 |
| 5,521,155 | 5/1996 | Malabarba et al. | 514/8 |
| 5,539,087 | 7/1996 | Restelli et al. | 530/412 |
| 5,567,676 | 10/1996 | Selva et al. | 514/8 |
| 5,594,102 | 1/1997 | Panzone et al. | 530/317 |
| 5,602,229 | 2/1997 | Malabarba et al. | 530/317 |
| 5,606,036 | 2/1997 | Hermann et al. | 536/4.1 |
| 5,644,025 | 7/1997 | Malabarba et al. | 530/317 |
| 5,674,840 | 10/1997 | Malabarba et al. | 514/9 |
| 5,750,509 | 5/1998 | Malabarba et al. | 514/11 |
| 5,863,679 * | 12/1998 | Selva et al. | 435/71.3 |
| 5,869,449 * | 2/1999 | Malabarba et al. | 514/11 |
| 5,939,523 * | 8/1999 | Bossi et al. | 530/317 |

FOREIGN PATENT DOCUMENTS

| | | |
|---|---|---|
| 0 184 625 | 6/1986 | (EP) . |
| 0 204 179 | 12/1986 | (EP) . |
| 0 290 922 | 5/1987 | (EP) . |
| 0 241 578 | 10/1987 | (EP) . |
| 0 276 740 | 8/1988 | (EP) . |
| 0 306 712 | 5/1989 | (EP) . |
| 0 326 873 | 8/1989 | (EP) . |
| 0 351 597 | 1/1990 | (EP) . |
| 0 351 684 | 1/1990 | (EP) . |
| 0 351 685 | 1/1990 | (EP) . |
| 0 352 538 | 1/1990 | (EP) . |
| 0 370 283 | 5/1990 | (EP) . |
| 0 448 940 | 10/1991 | (EP) . |
| 0 505 735 | 9/1992 | (EP) . |
| 0 525 499 | 2/1993 | (EP) . |

* cited by examiner

CHEMICAL PROCESS FOR PREPARING AMIDE DERIVATIVES OF ANTIBIOTIC A 40926

The present invention refers to an improved chemical process for preparing amide derivatives of antibiotic A 40926 of formula I:

[Structure of formula I shown]

wherein:
- $R_1$ represents $(C_9-C_{12})$alkyl;
- M represents hydrogen, α-D-mannopyranosyl or 6-O-acetyl-α-D-mannopyranosyl;
- Y represents an amino group of formula $$-NR_2\text{-alk}_1\text{-}(NR_3\text{-alk}_2)_p\text{-}(NR_4\text{-alk}_3)_q\text{-W}$$

wherein:
- $R_2$ represents hydrogen or $(C_1-C_4)$alkyl;
- $alk_1$, $alk_2$ and $alk_3$ each independently represent a linear or branched alkylene of 2 to 10 carbon atoms;
- p and q are integers which independently represent zero or 1;
- $R_3$ and $R_4$ each independently represent hydrogen, $(C_1-C_4)$alkyl or
- $R_2$ and $R_3$ taken together represent a $(C_2-C_4)$alkylene moiety connecting the two nitrogen atoms with the proviso that p is 1; or
- $R_3$ and $R_4$ taken together represent a $(C_2-C_4)$alkylene moiety connecting the two nitrogen atoms with the proviso that both p and q are 1;
- W represents hydrogen, $(C_1-C_4)$alkyl, amino, $(C_1-C_4)$alkylamino, di$(C_1-C_4)$alkylamino, amino substituted with one or two amino$(C_2-C_4)$alkylene moieties or with one or two $(C_1-C_4)$alkylamino-$(C_2-C_4)$alkylene moieties or with one or two di$(C_1-C_4)$alkylamino-$(C_2-C_4)$alkylene moieties, or, when both p and q are zero, taken together with the moiety —$NR_3$-$alk_1$- it may also represent piperazino or 4-methylpiperazino.

Antibiotic A 40926 is a glycopeptide antibiotic complex which has been isolated from a culture of Actinomadura, named Actinomadura sp. ATCC 39727, in a culture medium containing assimilable sources of carbon, nitrogen, and inorganic salts (see U.S. Pat. No. 4,935,238). According to the procedure described in the above cited patent the recovery of the antibiotic complex, whose major factors have been named factor A, factor B, factor $B_0$, factor $B_1$, factor PA, and factor PB, includes submitting the fermentation broths, after filtration or after a preliminary purification, to affinity chromatography on immobilized D-alanyl-D-alanine.

The A 40926 factors so far identified can be represented by formula (II) below wherein R is carboxy, $R_1$ represents a $(C_9-C_{12})$alkyl group, and M represents an α-D-mannopyranosyl or a 6-O-acetyl-α-D-mannopyranosyl group.

[Structure of formula II shown]

More particularly, antibiotic A 40926 factor A is a compound of the above formula (II) wherein R is carboxy, $R_1$ represents n-decyl, and M represents α-D-mannopyranosyl. According to the most recent studies, the substance identified in the above mentioned EP-177882 as antibiotic A 40926 factor B, actually consists of two closely related components. Antibiotic A 40926 factor $B_0$ is indeed the main component of factor B, and corresponds to the compound of the above formula (II) wherein R is carboxy, $R_1$ represents 9-methyldecyl, and M represents α-D-mannopyranosyl.

The minor component of factor B is named factor $B_1$ and differs from factor $B_0$ only in that $R_1$ represents n-undecyl (E. Riva et al, Chromatographia, Vol. 24, 295, 1987).

Antibiotic A 40926 factor PA and factor PB differ from the corresponding factor A and B in that the mannose unit is replaced by a 6-O-acetyl-α-D-manno-pyranose unit.

Antibiotic A 40926 factors PA and PB, at least under certain fermentation conditions, are the main antibiotic products of the A 40926 producing microorganism.

Antibiotic A 40926 factors A and B are mainly transformation products of antibiotics A 40926 factor PA and factor PB, respectively, and are often already present in the fermentation broths.

It has been found that antibiotic A 40926 factor PA can be transformed into antibiotic A 40926 factor A and antibiotic A 40926 factor PB can be transformed into antibiotic A 40926 factor B under basic conditions which lead to the removal of the acetyl group of the mannose unit without displacing the acyl group on the aminoglucuronyl unit.

As a consequence, when the fermentation broth or an antibiotic A 40926 containing extract or concentrate thereof, is allowed to stand for a certain time under basic conditions (e.g. aqueous solution of a nucleophilic base, at a pH>9 overnight) an antibiotic A 40926 complex is obtained which is enriched in antibiotics A 40926 factor A and factor B.

During the usual purification procedures of antibiotic A 40926 complex, factors PA and PB are largely converted to factors A and B.

Antibiotic A 40926 factor B can be obtained from A 40926 complex by chromatographic separation using the method described in U.S. Pat. No. 4,935,238. Pure factor $B_0$ which under the conditions described in the above mentioned European Patent account for about 90% of factor B, can be obtained by further purification of factor B, for instance, by repeated reverse-phase chromatography procedures.

More recent studies (L. Zerilli et al., Rapid Communications in Mass Spectrometry, Vol. 6, 109, 1992) have shown that in the antibiotic complex A 40926 also some minor factors are present, which have been identified with the acronyms $A_1$, RS-1, RS-2 and RS-3. These minor factors have been individuated by HPLC and their structures have been determined by applying gas chromatography/mass spectrometry analysis of the methanolysates of the A-40926 complex.

All the above mentioned minor factors have structures corresponding to the basic structure of factor A, $B_0$ and $B_1$ apart from the fatty acid residues linked to the aminoglucuronic moiety. More particularly, making reference to the formula (II), R has the same meanings as above while $R_1$ represents: 8-methylnonyl in factor $A_1$, 7-methyloctyl in factor RS-1, n-nonyl in factor RS-2 and n-dodecyl in factor RS-3.

Although in the preparations of antibiotic A 40926 complex currently carried out under the fermentation conditions described in U.S. Pat. No. 4,935,238 the factors wherein $R_1$ is a $(C_{10}-C_{11})$alkyl are largely predominant, it is possible to modify the fermentation conditions to increase the amounts of the minor components wherein $R_1$ is a $C_9$ or a $C_{12}$ alkyl.

All the sugar moieties are linked to the antibiotic A 40926 nucleus through O-glycosidic bonds.

In addition, it has been found that it is possible to transform antibiotic A 40926 complex, its single factors or a mixture of said factors in any proportion into the corresponding de-mannosyl derivatives (i.e. N-acylaminoglucuronyl aglycone complex AB, N-acylaminoglucuronyl aglycone factor A, N-acylaminoglucuronyl aglycone factor B) by controlled acid hydrolysis of the mannosyl sugar moiety of the starting material (see U.S. Pat. No. 4,868,171).

Preferred hydrolysis conditions for the production of N-acylaminoglucuronyl aglycones comprise the usage of a mixture of dimethylsulfoxide/concentrated hydrochloric acid from 8:2 to 9.5:0.5 at a temperature between 40° C. and 80° C.

Antibiotic A 40926 N-acylaminoglucuronyl aglycones are represented by the above formula (II) wherein M is hydrogen, R is carboxy and $R_1$ is $(C_9-C_{12})$alkyl.

Antibiotic A 40926 complex, the factors thereof, the corresponding N-acylaminoglucuronyl aglycones and mixtures thereof in any proportion are mainly active against gram positive bacteria and Neisseriae.

For the purposes of the present invention, each one of the above factors or hydrolytic derivatives of antibiotic A 40926 may be employed as starting materials for the present amidation process, either as a single substance or as a mixture of two or more of them in any proportion. The term "mixtures" refers to the A 40926 complex obtained from a standard or modified fermentation process as known in the art, to the demannosylated A 40926 complex thereof, to a complex obtained by applying particular conditions in the isolation/purification of the A 40926 complex or demannosylated A 40926 complex or to mixtures obtained by mixing in the appropriate proportion the single factors of the A 40926 complex and/or the hydrolyzed factors thereof, previously isolated by means of chromatographic separation procedures.

International Pat. Appl. Publ. No. WO 92/17495, (designating also U.S.), describes ester derivatives of antibiotic A 40926 (esterified at the position $6^B$, that is the carboxy group present on the N-acylamino glucuronyl moiety) and its de-mannosyl derivatives are described; e.g. the compounds of formula (II) wherein R is $(C_1-C_4)$ alkoxycarbonyl and R. and M have the same meanings of the symbols $R_1$ and M of formula I.

These ester derivatives are prepared by reacting the $N^{15}$-protected (in this description the term "$N^{15}$" refers to the nitrogen atom of the amino function linked to the carbon atom at the 15-position of A 40926 molecule) or $N^{15}$-free amino A 40926 substrate or its demannosyl derivative with an alkanol in an acid medium, or a $N^{15}$-protected A 40926 derivative or its demannosyl analogue with an alkyl halide (preferably bromide, chloride or iodide), optionally, in the presence of an hydrohalic acid acceptor, in particular, with an excess of the selected alkanol in the presence of concentrated mineral acid at a temperature between 0° C. and room temperature.

The above ester derivatives of antibiotic A 40926 obtainable from the A 40926 starting material as above specified (single factors or mixtures thereof) are employed as intermediate compounds in the process disclosed in the International Patent Appl. Publ. No. WO 93/03060 (designating also U.S.) for preparing amide derivatives of antibiotic A 40926; among the amide derivatives of A 40926 disclosed therein, WO 93/03060 discloses also the amide derivatives of formula I, together with a specific process for obtaining them.

The amidation process reported in WO 93/03060 for preparing the compounds of formula I consists essentially of 5 steps, which can be summarized as follows:
a) Preparation of an ester derivative on the $6^B$-carboxy function of A 40926;
b) protection of the amine function at the $N^{15}$-position;
c) reduction of the ester moiety at the $6^B$-position;
d) deprotection of the amine function at the $N^{15}$-position;
e) amidation reaction on the $C^{63}$-carboxy function of A 40926.

Alternatively, steps c) and d) may be carried out after step e), i.e. the reduction of the ester moiety and the deprotection of the amine function may be carried out after the amidation reaction. The amidation according to the process disclosed in WO 93/03060 is carried out either in the presence of a condensing agent or via formation of an activated ester on the $C^{63}$-carboxy group.

According to WO 93/03060, the so obtained amide derivative is then recovered and purified by reverse phase column chromatography on silanized silica gel, eluting with acetonitrile/acetic acid mixtures.

In this description and claims, when it is not otherwise specified, the term "alkyl", either alone or in combination with other substituents, includes both straight and branched hydrocarbon groups; more particularly, the term "$(C_1-C_4)$ alkyl" represents a straight or branched aliphatic hydrocarbon chain of 1 to 4 carbon atoms such as methyl, ethyl, propyl, 1-methylethyl, butyl, 1-methylpropyl, 1,1-dimethylethyl, and 2-methylpropyl.

As used herein, the terms "$alk_1$", "$alk_2$" and "$alk_3$" represent an independent linear or branched bifunctional aliphatic chain of 2 to 10 carbon atoms such as for example:
—$CH_2$—$CH_2$—,
—$CH_2$—$CH_2$—$CH_2$—,
—$CH_2$—$CH_2$—$CH_2$—$CH_2$—,
—$CH_2$—$CH_2$—$CH_2$—$CH_2$—$CH_2$—,
—$CH_2$—$CH_2$—$CH_2$—$CH_2$—$CH_2$—$CH_2$—,
—$CH_2$—$CH_2$—$CH_2$—$CH_2$—$CH_2$—$CH_2$—$CH_2$—,
—$CH_2$—$CH_2$—$CH_2$—$CH_2$—$CH_2$—$CH_2$—$CH_2$—$CH_2$—,
—$CH_2$—$CH_2$—$CH_2$—$CH_2$—$CH_2$—$CH_2$—$CH_2$—$CH_2$—$CH_2$—,
—$CH_2$—$CH_2$—$CH_2$—$CH_2$—$CH_2$—$CH_2$—$CH_2$—$CH_2$—$CH_2$—$CH_2$—,

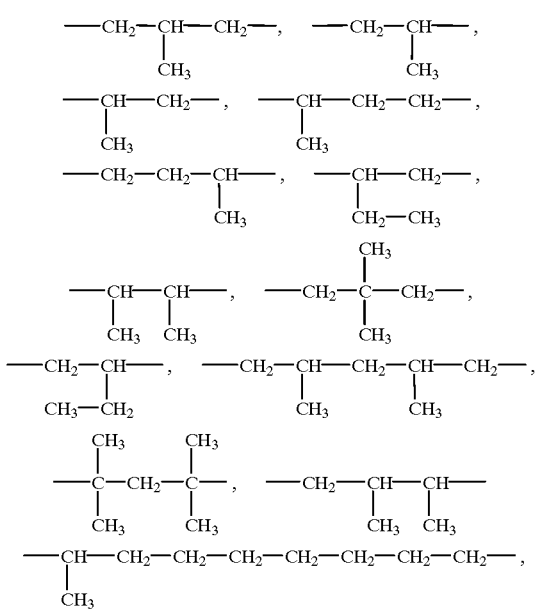

The term "$(C_2-C_4)$alkylene moiety" as used herein represents a linear or branched bifunctional aliphatic chain of 2 to 4 carbon atoms. Representative examples of said chains can be drawn from the above list.

The expression "$(C_1-C_4)$alkoxycarbonyl" includes both straight and branched alkoxycarbonyl groups such as for instance methoxycarbonyl, ethoxycarbonyl, propyloxycarbonyl, isopropyloxycarbonyl, butoxycarbonyl, isobutoxycarbonyl, and tert-butoxycarbonyl.

Here below are given some representative examples of the amino group

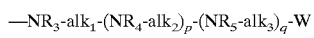

according to the above definition:

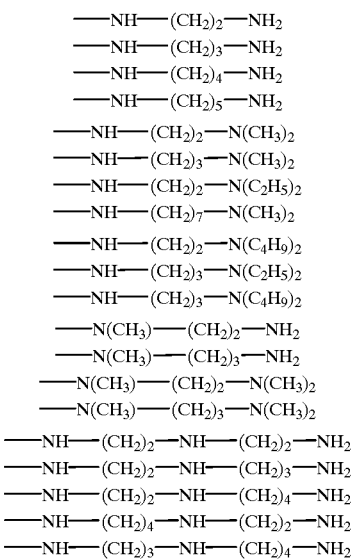

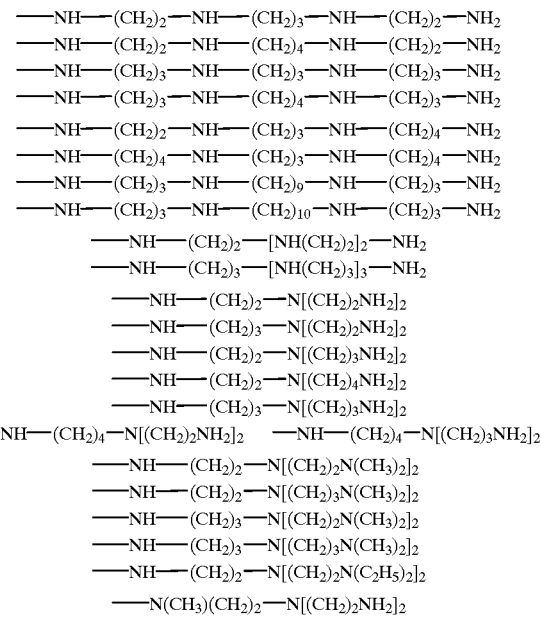

—NH—$(CH_2)_n$—$CH_3$ n = 0, 1, 2, 3, 4 or 5

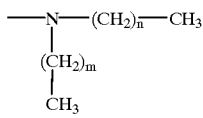

n = 0, 1, 2, 3, 4 or 5
m = 0, 1, 2 or 3

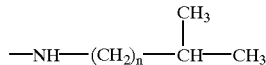

n = 0, 1, 2, or 3

—NH—$(CH_2)_n$—$NHCH_3$ n = 2, 3, or 4

—NH—$(CH_2)_n$—$NHiC_3H_7$ n = 2, 3, or 4

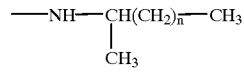

n = 0, 1, 2 or 3

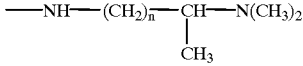

n = 1, 2 or 3

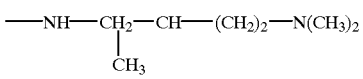

n = 1, 2, or 3

—NH($CH_3$)—$(CH_2)_n$—$NHCH_3$ n = 2, 3 or 4

—N$(CH_2)_n$—$NHC_2H_5$ n = 2, 3, or 4 and the like.

When $R_3$ and $R_4$ (or $R_4$ and $R_5$) taken together represent a $(C_2-C_4)$alkylene moiety connecting the two nitrogen atoms, the saturated heterocyclic moiety formed in combination with the portions $alk_1$ (or $alk_2$) and the two adjacent nitrogen atoms is preferably a piperazino ring.

For example, when $R_3$ and $R_4$ (or $R_4$ and $R_5$) taken together represent a $(C_2-C_4)$alkylene moiety connecting the two nitrogen atoms or when, both p and q being zero, W taken together with the moiety —$NR_3$-$alk_1$- represents piperazino or 4-methylpiperazino, the amino group of formula:

—$NR_3$-$alk_1$-$(NR_4$-$alk_2)_p$-$(NR_5$-$alk_3)_q$-W identifies the following groups:

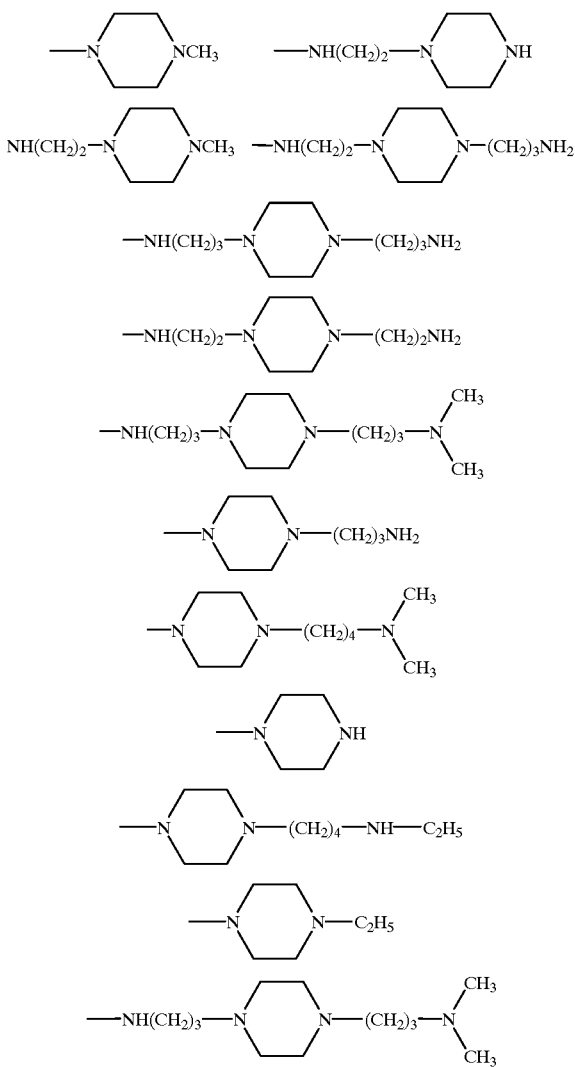

As said above, the present invention provides an improved process for preparing the compounds of formula I. Said process involves a lower number of reaction's steps with respect to the process disclosed in WO 93/03060, and further improvements relating both to the amidation step and to the purification of the crude product of formula I, for increasing the total yield of the process.

In particular, it has been found that the protection of the amino group at the 15-position (step b) can be avoided without negatively affecting the process course, while steps a) and c) can conveniently be carried out in a one-pot reaction.

Furthermore, it has been found that, when the amidation step is carried out in the presence of a condensing agent, it is possible to improve the reaction's yields by controlling the reaction conditions; in particular, attention should be paid in setting the initial pH of the reacting mixture, while also the amount of condensing agent and the amount of amine reactant may be adjusted for improve the reaction's yield and minimize the formation of side-products.

In addition, a particularly advantageous chromatographic purification procedure has been set up, which involves the adsorbtion of the compound of formula I onto a polyamide resin and wherein only aqueous solutions are employed for the preliminar washings of the resin and the elution of the product.

Thus, one aspect of the present invention refers to the preparation of the intermediate compound of formula III:

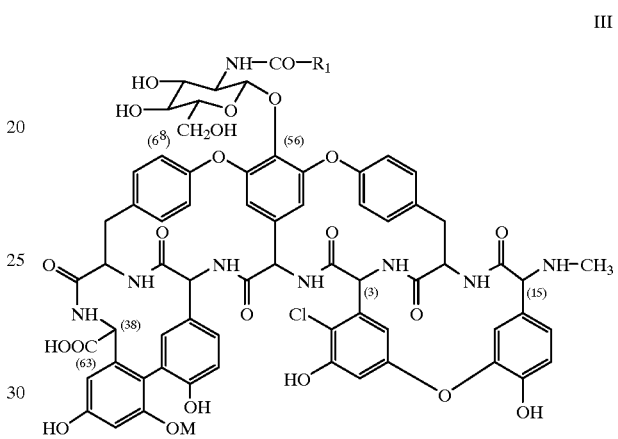

wherein $R_1$ and M are as defined in formula I, by reacting a compound of formula II

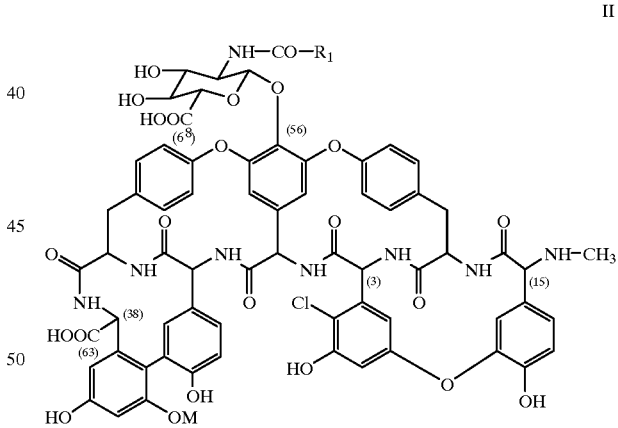

wherein $R_1$ and M are as above defined, with a $(C_1-C_4)$ alkanol in the presence of a concentrated mineral acid, using the same alkanol as the reaction solvent and submitting the obtained ester compound to a reductive process by adding an alkali metal borohydride into the same reaction mixture.

A further aspect of the present invention refers to the amidation reaction for obtaining the compound of formula I; this is carried out by reacting a compound of formula III with a suitable amine of formula IV $NHR_3$-$alk_1$-$(NR_4$-$alk_2)_p$-$(NR_5$-$alk_3)_q$-W          IV wherein $R_3$, $R_4$, $R_5$, $alk_1$, $alk_2$, $alk_3$, p, q and W are as defined in formula I, in an inert organic solvent, in the presence of a condensing agent and setting the initial pH of the mixture (measured after diluting a sample of the reaction mixture with 9 volumes of water) at a value of from 6.5 to 9.0.

Furthermore, by combining the above improved steps into a single process, it is possible to set up a new particularly convenient process for preparing the compounds of formula I, which comprises:

a) reacting a compound of formula II with a ($C_1$–$C_4$) alkanol in the presence of a concentrated mineral acid, using the same alkanol as the reaction solvent;

b) submitting the obtained compound to a reductive process with an alkali metal borohydride, in the same reaction mixture, thus obtaining a compound of formula III;

c) reacting a compound of formula III with a suitable amine of formula

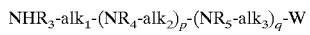

in an inert organic solvent, in the presence of a condensing agent and setting the initial pH of the mixture (measured after diluting a sample of the reaction mixture with 9 volumes of water) at a value of from 6.5 to 9.0.

The reaction of a compound of formula II with a ($C_1$–$C_4$) alkanol can be carried out by following the process disclosed in WO 93/03060. Accordingly, the A 40926 starting material is contacted with an excess of the seleted ($C_1$–$C_4$)alkanol in the presence of a concentrated mineral acid at a temperature of from 0° C. to room temperature, for a time varying from 4 to 24 hours.

The ($C_1$–$C_4$)alkanol is selected from methanol, ethanol, propanol and butanol; preferably, ethanol is employed. As the alkanol acts both as reactant and as solvent, an excess of it is employed for the esterification reaction. Its molar amount may vary from 300 and 3000 times the amount of the A 40926 starting material; preferably an excess of from 500 to 1500 moles is employed, particularly preferred being an excess of about 650 moles.

Concentrated mineral acids are those known in the art, such as concentrated sulfuric or hydrochloric acid. The acid is preferably added to an alkanolic solution of the A 40926 starting material as a solution with the same alkanol. In general, the final concentration of the acid in the alkanolic reaction mixture will vary from 5 to 10% (w/v), preferably being about 7%, while the molar amount of acid will vary from 15 to 50 times the molar amount of the A 40926 starting material, preferably about 20 times.

The alkanolic solution is generally cooled at about 0° C. before the addition of the mineral acid, and the temperature is preferably kept at about 0°–5° C. for a short time after the addition of the acid; then the temperature is preferably allowed to rise during the esterification reaction at about 20° C., while stirring the reaction mixture.

The reaction course is monitored by means of the conventional analytical techniques, for determining when the esterification reaction is completed; for this purpose, HPLC analysis is preferably employed. The reaction time will depend from the temperature, the amount of alkanol and the concentration of the acid; for instance, when the molar amount of alkanol is about 650 times the amount of A 40926 starting material, the molar amount of acid is about 20 times, and the temperature is about 20° C., the reaction may generally considered completed after about 18 hours from the addition of the acid to the alkanolic solution of the A 40926 starting material.

When the esterification reaction is completed, before the reduction step with alkali metal borohydride, the pH of the mixture is preferably adjusted at a value of about 4.5–7.0 by addition of an aqueous alkaline solution, preferably after having cooled the reaction mixture down to about 0° C. to 5° C. Suitable solutions for adjusting the pH are aqueous carbonate, bicarbonate or hydroxide solutions, in particular aqueous $Na_2CO_3$, $NaHCO_3$ or $NaOH$ solutions; preferably an aqueous solution of $Na_2CO_3$ is employed.

The so obtained hydro-alcoholic mixture is then treated with an alkali metal borohydride, for reducing the ester group at position $6^B$ of the A 40926 molecule. The so obtained hydro-alchoholic mixture is then treated with an alkali metal borohydride, reducing the ester group at position $6^B$ of the A 40926 molecule, and thus obtaining the compound of formula III.

Examples of suitable alkali metal borohydride are lithium borohydride, sodium borohydride, magnesium borohydride, sodium trimethossiborohydride or sodium cyanoborohydride; particularly preferred is sodium borohydride.

The amount of the alkali metal borohydride will vary from 5 or 8 to 50 times the molar amount of the A 40926 ester derivative. Preferably an excess from 8 or 10 to 16 times is employed, particularly preferred being an excess of 12 times.

The reaction course is monitored by means of the conventional analytical techniques, for determining when the reduction is completed; also in this case, HPLC analysis is preferably employed. The reaction is generally completed in about 1 to 6 hours, depending on the temperature and the excess of reducing agent.

When the reaction is completed, the excess of reducing agent is neutralized (for instance by addition of acetone) and the mixture is treated according to the known techniques for obtaining the crude compound of formula III.

The amidation reaction is then carried out by reacting the compound of formula III with the desired amine of formula IV, in an inert organic solvent, in the presence of a condensing agent. As said above, a critical reaction's parameter is the pH of the mixture, which should be adjusted at the beginning at a value of about 6.5–9.0 (measured after diluting the reaction mixture with 9 volumes of water), preferably from about 7.5 to 8.2.

The amine is preferably reacted in excess with respect to the intermediate compound of formula III, preferably from 1.6 to 2.2 moles per mole of intermediate, particularly preferred being about 1.8 moles per mole of intermediate.

For carrying out the amidation in the presence of a condensing agent, it is necessary that the amine reactant be capable of forming a salt with the 63-carboxy function of the compound of formula III. In case the amine is not strong enough to form such a salt in the selected reaction medium, it is necessary to add a salt-forming base (e.g. a tertiary aliphatic or heterocyclic amine, such as triethylamine (TEA), N-methylpyrrolidine or N-methyl-piperazine, which cannot form an amide bond with the carboxy function) to the reaction mixture in an at least equimolecular amount with respect to the A 40926 compound; a preferred salt-forming base is TEA.

Use of a low molar excess of the amine reactant with addition of a salt-forming base is a suitable method when the amine reactant is a rather expensive or difficult to obtain product.

It should be pointed out that, in general, the excess of amine added to the reaction mixture will normally keep the pH above the suitable value; thus, for adjusting the pH at the desired value, a mineral acid preferably diluted in an inert organic solvent can conveniently be added to the mixture. Examples of suitable mineral acids are hydrochloric, sulfuric and phosphoric acid, while examples of inert organic solvents are dimethylformamide, dimethylsufoxide and dimethoxyethane; for instance a solution of 27% hydrogen chloride in dimethylformamide or dimethylsulfoxide can suitably be employed.

Alternatively, the amine reactant may also be conveniently introduced in the reaction medium as a corresponding acid addition salt, e.g. the hydrochloride. In this case a molar excess of a strong base capable of freeing the amine from its salts is added; the added excess should be such to allow the initial pH of the mixture to be in the above range 6.5–9.0. Also in this case, the suitable base is usually a tertiary organic aliphatic or heterocyclic amine which cannot form an amide bond with carboxy functions like those exemplified above, preferably TEA. In fact, at least in some instances, the use of a salt of the amine which is then freed in situ with the above mentioned bases, is highly preferred, especially when the salt is more stable than the corresponding free amine.

Suitable inert organic solvents are those organic aprotic solvents which do not unfavourably interfere with the reaction course and are capable of at least partially solubilizing the starting material.

Examples of said inert organic solvents are organic amides, ethers of glycols and polyols, phosphoramides and sulfoxides. Preferred examples of inert organic solvents are: dimethylformamide (DMF), dimethoxyethane, hexamethylphosphoramide, dimethylsulfoxide (DMSO) and mixtures thereof. Preferably, DMSO is employed.

The condensing agent employed in the amidation process of the invention is one suitable for forming amide bonds in organic compounds and in particular in peptide synthesis.

Representative examples of condensing agents are diisopropylcarbodiimide (DIC), dicylcohexylcarbodiimide (DCC) in the presence of hydroxybenzotriazole (HBT), benzotriazolyloxy-tris-(dimethylamino)phosphonium hexafluorophosphate, benzotriazolyloxy-tris-(pyrrolidino) phosphonium hexafluorophosphate and ($C_1$–$C_4$)alkyl, phenyl or heterocyclic phosphorazidates such as diphenyl phosphorazidate, diethyl phosphorazidate, di-(4-nitrophenyl)phosphorazidate, dimorpholylphosphorazidate and diphenylphosphoro-chloridate. The preferred condensing agents are diphenyl phosphorazidate, i.e. phosphoric acid diphenyl ester azide (DPPA), benzotriazolyloxy-tris-(dimethylamino)phosphonium hexafluorophosphate (BOP), and benzotriazolyloxy-tris-(pyrrolidino)phosphonium hexafluorophosphate (PyBOP).

Between the two last mentioned condensing agents PyBOP is particularly preferred since the resulting by-product pyrrolidine has less potential toxicity problems than dimethylamine.

The amount of condensing agent may vary from 1 to 1.8 moles per mole of compound III, preferably being about 1.4 moles.

The reaction temperature will vary considerably depending on the specific starting materials and reaction conditions.

In general, it is preferred to conduct the reaction at a temperature between 0–30° C., preferably at about 5° C.

Also the reaction time will vary considerably depending on the condensing agent and the other reaction parameters, such as temperature, molar amount of the reacting amine and steric complexity of it. In general, the condensation reaction is completed within a period of time from about one hour to about 24–48 hours.

In any case, the reaction course is monitored by TLC or, preferably, by HPLC according to methods known in the art.

On the basis of the results of these assays a man skilled in the art will be able to evaluate the reaction course and decide when to stop the reaction and start working up the reaction mass.

The compound of formula I is then recovered as a crude product according to known per se techniques which include, for instance, extraction with solvents, precipitation by addition of non-solvents, etc.. Preferably, the crude product is recovered by precipitation from the reaction mixture, for instance by addition of a non-solvent such as acetone, ethylacetate and the like, followed by filtration of the crude precipitate.

As previously stated, the present invention further provides an improved purification process for purifying the crude amide derivative of formula I obtainable according to the above amidation process. Said purification process comprises:
  a) dissolving the crude product of formula I into an aqueous acid buffered solution;
  b) adsorbing said compound onto a polyamide resin;
  c) washing the resin with the above aqueous acid buffered solution and then with an aqueous basic solution;
  d) eluting the compound with an aqueous acid solution and collecting those fractions containing the purified compound of formula I.

The aqueous acid buffered solution referred to in step a) should be such as to completely solubilize the crude compound of formula I, while the buffer's constituents, apart from their solubilizing effect, shall not (or, in any case, only reversibly) interact with the compound of formula I. Furthermore, as the same buffer is employed in step c) for the first resin's washing, it should be such as to not (or only minimally) elute the desired compound during the washing. Accordingly, preferred aqueous acid buffered solutions are those having a pH value from about 3.6 to about 4.2, preferably from 3.8 to 4.0, particularly preferred being a buffered solution having a pH value of about 3.9. Suitable buffers are solutions of organic acids with their respective alkali metal salts, such as acetate/acetic acid, formiate/formic acid; preferably, a sodium acetetate/acetic acid buffer is employed.

The aqueous basic solution referred to in step c) should be such as to remove basic impurities adsorbed on the resin. Preferred solutions are those having a pH value from about 8.5 to 9.2, preferably from 8.8 to 9.0, particularly preferred being solutions having a pH value of about 8.9. Suitable basic solutions are alkali metal salts of organic acids such as acetate or formiate; preferably sodium acetate is employed.

The aqueous acid solution referred to in step d) should be such as to completely elute the compound of formula I adsorbed on the resin. Preferred solutions are those having a pH value from about 3.2 to 3.6, preferably from 3.3 to 3.5, particularly preferred being solutions having a pH value of about 3.4. Suitable aqueous acid solutions may be prepared with organic acids such as acetic or formic acid; preferably acetic acid is employed.

Polyamide resins that have been found useful in the present purification process are selected from the polyamide column chromatography resins generally identified as polycaprolactame, nylons (6/6, 6/9, 6/10 and 6/12) and the cross-linked polyvinylpyrrolidone. Said chromatography polyamide resins are generally characterized by a pore volume ranging between 1 and 5 ml/g, surface area(*) ranging between 1 and 100 $m^2$/g, apparent density ranging between 0.15 and 0.50 g/ml, average pore diameter(*) ranging between 100 and 3000 Å and particles size distribution where at least 40 percent of the particles have size lower than 300 micron (*=measured with a mercury porosimeter model Serie 200 of C. Erba S.p.A., Milano Italy). Specific examples of commercially available polyamide column chromatography resins suitable for the embodiment of this invention are the polyamide resins Polyamide-CC 6, Polyamide-SC 6, Polyamide-CC 6.6, Polyamide-CC 6AC and Polyamide-SC 6AC of Macherey-Nagel & Co. (Germany), the polyvinylpyrrolidone resin PVP-CL of Aldrich Chemie Gmbh & Co., KG (Germany), the polyamide resin PA 400 of M. Woelm (Germany). Particularly suitable is the resin polyamide-SC 6 (Macherey-Nagel).

Although the above outlined purification process would be suitable for the purification of any crude compound of formula I, independently from whether it is obtained according to the amidation process of the invention or not, in view of the general improvements provided with the present invention, the skilled man will appreciate applying said purification process for preferably purifying the crude compounds of formula I obtained according to the improved amidation process disclosed above.

The so obtained compound would generally have a purity degree suitable for pharmaceutical use. Known per se recovery procedures may further be applied, such as ultrafiltration, together with further treatments of the product, for instance depyrogenation when an injectable product is desired.

Among the compounds defined by formula I, a group of preferred compounds which can be prepared according to the process of the present invention are those compounds of formula I wherein $R_1$ represents $(C_{10}–C_{11})$alkyl, M represents α-D-mannopyranosyl and Y is as defined in formula I.

Within the above group, particularly preferred are those compounds wherein Y represents an amino group of formula:

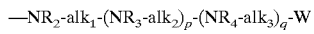

wherein:

$R_2$, $R_3$ and $R_4$ each independently represents hydrogen or $(C_1–C_4)$alkyl;

$alk_1$, $alk_2$ and $alk_3$ each independently represent a linear or branched alkylene of 2 to 10 carbon atoms;

p and q are integers which independently represent zero or 1;

W represents hydrogen, $(C_1–C_4)$alkyl, amino, $(C_1–C_4)$alkylamino, di$(C_1–C_4)$alkylamino, amino substituted with one or two amino$(C_2–C_4)$alkylene moieties or with one or two $(C_1–C_4)$alkylamino-$(C_2–C_4)$alkylene moieties or with one or two di$(C_1–C_4)$alkylamino-$(C_2–C_4)$alkylene moieties, or, when both p and q are zero, taken together with the moiety —$NR_3$-$alk_1$- it may also represent piperazino or 4-methylpiperazino.

A further preferred group of compounds of formula I which may be prepared according to the process of the present invention is defined by those compounds of formula I wherein: $R_1$ represents $(C_{10}–C_{11})$alkyl, M represents α-D-mannopyranosyl and Y represents an amino group of formula:

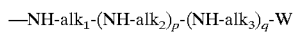

wherein:

$alk_1$, $alk_2$ and $alk_3$ each independently represent a linear or branched alkylene of 2 to 10 carbon atoms;

p and q are integers which independently represent zero or 1;

W represents hydrogen, $(C_1–C_4)$alkyl, amino, $(C_1–C_4)$alkylamino, di$(C_1–C_4)$alkylamino, amino substituted with one or two amino$(C_2–C_4)$alkylene moieties or with one or two $(C_1–C_4)$alkylamino-$(C_2–C_4)$alkylene moieties or with one or two di$(C_1–C_4)$alkylamino-$(C_2–C_4)$alkylene moieties.

The following examples are given to illustrate more in detail the improved process of the present invention.

HPLC analyses were performed using a HP 1090 M instrument equipped with a DAD system connected to a work station. All chromatograms were recorded at 254 nm following injection of 10 ml of solution. In particular:

a) for monitoring the esterification and reduction steps: BECKMAN Ultrasphere ODS 5 mm, 4.6×250 mm column at 40° C. with a flow rate of 1.5 ml/minute; linear gradient from 28% to 58% of acetonitrile (30 minutes) in buffered 0.02M $NaH_2PO_4$ (pH 6.5) as mobile phase;

b) for monitoring the amidation step: Asahipach ODP 50 5 μm, 4.6×250 mm column at 40° C. with a flow rate of 0.9 ml/minute; linear gradient from 26% to 56% of acetonitrile (25 minutes) in $NaH_2PO_4$ 0.05 M buffered (pH 3.2) as mobile phase;

c) for analysis of the purified product: Asahipach ODP 50 5 μm, 4.6×250 mm column and a Brownlee RP-18 7 μm. 3.2×15 mm pre-column at 40° C. with a flow rate of 0.9 ml/minute; acetonitrile (phase B) in $NaH_2PO_4$ 0.05 M buffered (pH 3.2) (35 min) as mobile phase, with the following gradient:

| Time(min) | 0 | 11 | 18 | 20 | 25 | 30 | 35 |
|---|---|---|---|---|---|---|---|
| % B | 26 | 33 | 33 | 40 | 43.5 | 54 | 26. |

The titre reported for the A 40926 complex (starting material or derivatives thereof) refers to the percentage (w/w) of factors $B_0+B_1$ (or corresponding derivatives thereof) with respect to the total amount of dry sample.

EXAMPLE 1

Preparation of the intermediate compound of formula III wherein $R_1$ is $(C_9–C_{12})$alkyl and M is α-D-mannopyranosyl 5 Kg of A 40926 complex obtained according to U.S. Pat. No. 4,935,238 (HPLC titre=65.4%, corresponding to about 1.88 moles) and 37.5 l of absolute ethyl alcohol are loaded under stirring at room temperature in a 140 l glass lined reactor. The resulting suspension is cooled to 0° C. and then a solution containing 2 l of sulfuric acid in 12 l of absolute ethanol is added in 30 minutes maintaining the internal temperature between 0–5 ° C.

The temperature is then left to rise at 20° C. while stirring is continued for an additional 18 hours. After this time the mixture is cooled again at 0–5° C. and adjusted to pH 5.8 by slowly adding 35 l of a 10% aqueous sodium carbonate solution.

The mixture is then transferred into a 230 l stainless steel reactor and 850 g of sodium borohydride (22.4 moles) dissolved in 9 l of water is slowly added, under stirring, with a peristaltic pump.

Stirring is continued at 5° C. for an additional two hours while the reduction is monitored by HPLC each hour by diluting a sample with 50 parts of water.

The excess of reducer is completely destroyed with 3 l of acetone and the resulting mixture is adjusted to pH 4.2 with 30% $H_2SO_4$. The suspension is then concentrated under vacuum at 40° C. to remove the organic solvents and the residue is diluted with 50 l of water and filtered under pressure (nitrogen 1.5 bar) on a stainless steel filter. The solid product is washed with 50 l of water and dried in a screw dryer under vacuum at 40° C. for 48 hours obtaining the title compound.

The above procedure is repeated on the same amount of A40926 starting material (5 Kg, titre 65.4%), using the same reactor.

A total amount of 8.91 Kg of the crude title compound is obtained (titre about 60%) with a molar yield of 82.2%.

EXAMPLE 2

Preparation of the 63-(dimethylaminopropyl)amido derivative of antibiotic A 40926 (compound of formula I wherein Y is the group —NH—$(CH_2)_3$—$N(CH_3)_2$, $R_1$ is $(C_9-C_{12})$alkyl and M is α-D-mannopyranosyl)

4.2 Kg of the crude compound obtained according to Example 1, 21.6 l of DMSO and 5.4 l of DMF are loaded in a 140 l glass lined reactor and the mixture is stirred until complete solubilization (90 minutes). Then 425 ml of dimethylaminopropilamine are added in 10 minutes and its pH, measured after diluting a sample 9:1 with water, is adjusted to 8 by adding 310 ml of a previously prepared 27% HCl(g)/DMF solution.

The mixture is cooled at 5° C. and then a solution, prepared by dissolving 1.12 Kg of PyBOP in 4.5 l of DMF, is added in 20 minutes at room temperature.

Stirring is continued for an additional hour, then the mixture is transferred in a 700 l glass lined reactor where the final product is precipitated with 150 l of ethyl acetate.

The suspension is filtered on a stainless steel filter and the solid obtained is washed on the filter with 30 l of ethyl acetate and dried in a stainless steel screw drier at 35° C. under vacuum for 24 hours, obtaining the title compound as a crude.

The above procedure is repeated on the same amount of A40926 starting material, using the same reactor.

A total amount of 10.4 Kg of the crude title compound is thus obtained (titre about 38%) with a molar yield of 76.0%.

EXAMPLE 3

Chromatographic purification of the 63-(dimethylaminopropyl)amido derivative of antibiotic A 40926 obtained according to Example 2.

900 g of the above crude material are dissolved in acetate buffer pH 3.9 (about 30 l ) and applied on the top of a chromatographic column (ID=30 cm), filled with about 56.5 l of polyamide resin (SC-6, Machery-Nagel) previously equilibrated with about 180 of the same acetate buffer.

The column is washed with about 120 l of the same acetate buffer and then with about 400 l of a 0.1 M sodium acetate solution (pH=8.9).

The compound of formula I is then eluted with about 400 l of acetic acid 0.1 M (pH 3.4), monitoring each fraction by HPLC and collecting those fractions containing the title compound (chromatographic yield about 80%).

What is claimed is:
1. Process for preparing a compound of formula I,

I wherein:

$R_1$ represents $(C_9-C_{12})$alkyl;

M represents hydrogen, α-D-mannopyranosyl or 6-O-acetyl-α-D-mannopyranosyl;

Y represents an amino group of formula —$NR_2$-$alk_1$-$(NR_3-alk_2)_p$-$(NR_4-alk_3)_q$-W wherein:

$R_2$ represents hydrogen or $(C_1-C_4)$alkyl;

$alk_1$, $alk_2$ and $alk_3$ each independently represent a linear or branched alkylene of 2 to 10 carbon atoms;

p and q are integers which independently represent zero or 1;

$R_3$ and $R_4$ each independently represent hydrogen, $(C_1-C_4)$alkyl or $R_2$ and $R_3$ taken together represent a $(C_2-C_4)$alkylene moiety connecting the two nitrogen atoms with the proviso that p is 1; or $R_3$ and $R_4$ taken together represent a $(C_2-C_4)$alkylene moiety connecting the two nitrogen atoms with the proviso that both p and q are 1;

W represents hydrogen, $(C_1-C_4)$alkyl, amino, $(C_1-C_4)$ alkylamino, di$(C_1-C_4)$ alkylamino, amino substituted with one or two amino-$(C_2-C_4)$alkylene moieties or with one or two $(C_1-C_4)$alkylamino-$(C_2-C_4)$alkylene moieties or with one or two di$(C_1-C_4)$alkylamino-$(C_2-C_4)$alkylene moieties, or, when both p and q are zero, taken together with the moiety —$NR_2$-$alk_1$- it also represents piperazino or 4-methylpiperazino, which comprises reacting a compound of formula III

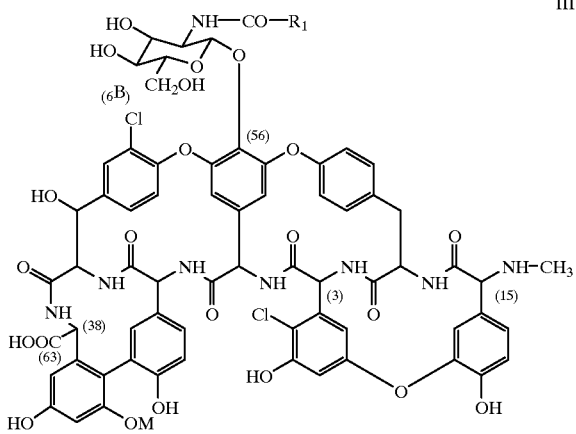

III wherein $R_1$ and M are as defined in formula I, with a suitable amine of formula IV

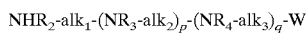

IV wherein $R_2$, $R_3$, $R_4$, $alk_1$, $alk_2$, $alk_3$, p, q and W are as defined in formula I, in an inert organic solvent, in the presence of a condensing agent, characterized in that the initial pH of the mixture, measured after diluting a sample of the reaction mixture with 9 volumes of water, is set at about 7.5–8.2.

2. Process according to claim 1 wherein a compound of formula III

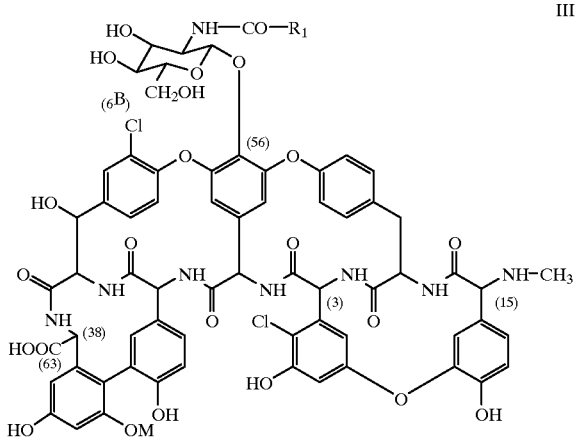

III wherein $R_1$ is $(C_9-C_{12})$alkyl and M is hydrogen, α-D-mannopyranosyl or 6-O-acetyl-α-D-mannopyranosyl, is prepared by a process which comprises reacting a compound of formula II

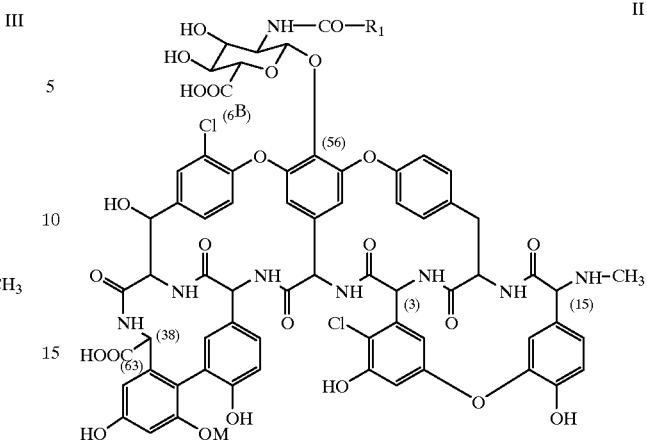

II wherein $R_1$ and M are as above defined, with a $(C_1-C_4)$ alkanol in the presence of concentrated mineral acid, using the same alkanol as a reaction solvent and submitting the obtained esterified compound to a reductive process by adding an alkali metal borohydride into the same reaction mixture.

3. Process according to claim 2 wherein the $(C_1-C_4)$ alkanol is ethanol.

4. Process according to claim 2 wherein the amount of alkanol is from 300 to 3000 times and the amount of mineral acid is from 15 to 50 times the molar amount of the compound of formula II.

5. Process according to claim 2 wherein the amount of alkanol is 650 times and the amount of mineral acid is about 20 times the molar amount of the compound of formula II.

6. Process according to claim 2 wherein the pH of the reaction mixture is adjusted to a value of about 4.5–7.0 before the reduction with alkali metal borohydride.

7. Process according to claim 2 wherein the alkali metal borohydride is sodium borohydride.

8. Process according to claim 2 wherein the amount of alkali metal borohydride is from 8 to 50 times the molar amount of the esterified compound.

9. Process according to claim 2 wherein the amount of alkali metal borohydride is about 12 times the molar amount of the esterified compound.

10. Process according to claim 1 wherein the amount of amine is from 1.6 to 2.2 times the molar amount of the compound of formula III.

11. Process according to claim 1 wherein the amount of amine is about 1.8 times the molar amount of the compound of formula III.

12. Process according to claim 1 wherein the condensing agent is selected from diisopropylcarbodiimide or dicyclohexylcarbodiimide in the presence of hydroxybenzotriazole; benzotriazolyloxy-tris-(dimethylamino)phosphonium hexafluorophosphate; -benzotriazolyloxy-tris-(pyrrolidino)-phosphonium hexafluorophosphate; and $(C_1-C_4)$alkyl, phenyl or heterocyclic phosphorazidates.

13. Process according to claim 1 wherein the condensing agent is benzotriazolyloxy-tris-(pyrrolidino)phosphonium hexafluorophosphate.

14. Process according to claim 12 wherein the amount of condensing agent is from 1 to 1.8 moles per mole of compound of formula III.

15. Process according to claim 12 wherein the amount of condensing agent is about 1.4 moles per mole of the compound of formula III.

16. Process according to claim 1 for preparing a compound of formula I wherein $R_1$ represents $(C_{10}–C_{11})$alkyl, M represents α-D-mannopyranosyl and Y is as defined in claim 1.

17. Process according to claim 16 wherein Y represents an amino group of formula:

wherein:

$R_2$, $R_3$ and $R_4$ each independently represents hydrogen or $(C_1–C_4)$alkyl;

$alk_1$, $alk_2$ and $alk_3$ each independently represent a linear or branched alkylene of 2 to 10 carbon atoms;

p and q are integers which independently represent zero or 1;

W represents hydrogen, $(C_1–C_4)$alkyl, amino, $(C_2–C_4)$ alkylamino, di$(C_1–C_4)$alkylamino, amino substituted with one or two amino $(C_2–C_4)$alkylene moieties or with one or two $(C_1–C_4)$alkylamino-$(C_2C_4)$alkylene moieties or with one or two di$(C_1–C_4)$alkylamino-$(C_2–C_4)$alkylene moieties, or, when both p and q are zero, taken together with the moiety —$NR_2$-$alk_1$- it also represents piperazino or 4-methylpiperazino.

18. Process according to claim 16 wherein Y represents an amino group of formula:

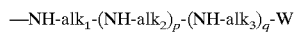

wherein:

$alk_1$, $alk_2$ and $alk_3$ each independently represent a linear or brached alkylene of 2 to 10 carbon atoms;

p and q are integers which independently represent zero or 1;

W represents hydrogen, $(C_1–C_4)$alkyl, amino, $(C_1–C_4)$ alkylamino, di$(C_1–C_4)$alkylamino, amino substituted with one or two amino$(C_2–C_4)$alkylene moieties or with one or two $(C_1–C_4)$alkylamino-$(C_2–C_4)$alkylene moieties or with one or two di$(C_1–C_4)$alkylamino-$(C_2–C_4)$alkylene moieties.

19. Process for preparing a compound of formula I,

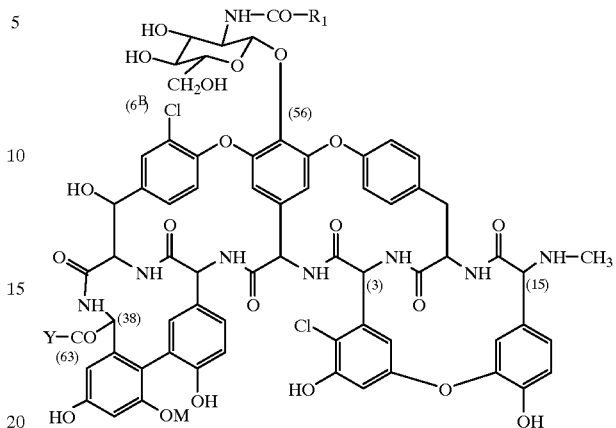

wherein:

$R_1$ represents $(C_9–C_{12})$alkyl;

M represents hydrogen, α-D-mannopyranosyl or 6-O-acetyl-α-D-mannopyranosyl;

Y represents an amino group of formula —$NR_2$-$alk_1$-$(NR_3$-$alk_2)_p$-$(NR_4$-$alk_3)_q$-W wherein:

$R_2$ represents hydrogen or $(C_1–C_4)$alkyl;

$alk_1$, $alk_2$ and $alk_3$ each independently represent a linear or branched alkylene of 2 to 10 carbon atoms;

p and q are integers which independently represent zero or 1;

$R_3$ and $R_4$ each independently represent hydrogen, $(C_1–C_4)$alkyl or $R_2$ and $R_3$ taken together represent a $(C_2–C_4)$alkylene moiety connecting the two nitrogen atoms with the proviso that p is 1; or $R_3$ and $R_4$ taken together represent a $(C_2–C_4)$alkylene moiety connecting the two nitrogen atoms with the proviso that both p and q are 1;

W represents hydrogen, $(C_1–C_4)$alkyl, amino, $(C_1–C_4)$ alkylamino, di$(C_1–C_4)$alkylamino, amino substituted with one or two amino-$(C_2–C_4)$alkylene moieties or with one or two $(C_1–C_4)$alkylamino-$(C_2–C_4)$ alkylene moieties or with one or two di$(C_1–C_4)$ alkylamino-$(C_2–C_4)$alkylene moieties, or, when both p and q are zero, taken together with the moiety —$NR_2$-$alk_1$- it also represents piperazino or 4-methylpiperazino, which comprises reacting a compound of formula III

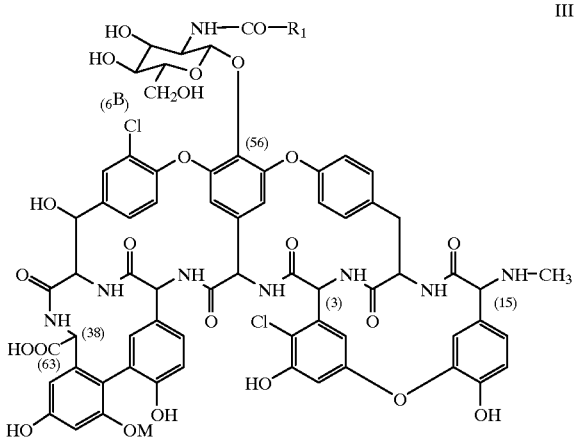

III wherein $R_1$ and M are as defined in formula I, with a suitable amine of formula IV

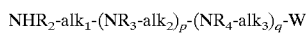

IV wherein $R_2$, $R_3$, $R_4$, $alk_1$, $alk_2$, $alk_3$, p, q and W are as defined in formula I, in an inert organic solvent, in the presence of a condensing agent, characterized in that the initial pH of the mixture, measured after diluting a sample of the reaction mixture with 9 volumes of water, is set at a value of from 6.5 to 9.0, and wherein the compound of formula I is purified according to the following sequence of steps:

a) dissolving the crude product of formula I into an aqueous acid buffered solution;
b) adsorbing said compound onto a polyamide resin;
c) washing, the resin with the above aqueous acid buffered solution and then with an aqueous basic solution;
d) eluting the compound with an aqueous acid solution and collecting those fractions containing the purified compound of formula I.

20. Purification process according to claim 19 wherein the polyamide resin is a polyamide column chromatography resin selected from polycaprolactame, nylons 6/6, 6/9, 6/10 and 6/12, and cross-linked polyvinylpyrrolidone.

21. Process according to claim 19 for purifying a compound of formula I wherein the aqueous acid buffered solution referred to in step a) and step c) has a pH value from about 3.6 to about 4.2.

22. Process according to claim 21 wherein the aqueous acid buffered solution referred to in step a) and step c) has a pH value from about from 3.8 to 4.0.

23. Process according to claim 21 wherein the aqueous acid buffered solution is an aqueous acetate/acetic acid or aqueous formate/formic acid buffered solution.

24. Process according to claim 19 for purifying a compound of formula I wherein the aqueous basic solution referred to in step c) has a pH value from about 8.5 to 9.2.

25. Process according to claim 24 wherein the aqueous basic solution has a pH value from about 8.8 to 9.0.

26. Process according to claim 24 wherein the aqueous basic solution is an acetate or formate solution.

27. Process according to claim 19 for purifying a compound of formula I wherein the aqueous acid solution referred to in step d) has a pH value from about 3.2 to 3.6.

28. Process according to claim 27 wherein the aqueous acid solution has a pH value from about 3.3 to 3.5.

29. Process according to claim 27 wherein the aqueous acid solution is an acetic or formic acid solution.

30. Purification process according to claim 20 wherein the polyamide resin is characterized by a pore volume ranging between 1 and 5 ml/g, surface area ranging between 1 and 100 m$^2$/g, apparent density ranging between 0.15 and 0.50 g/ml, average pore diameter ranging between 100 and 3000 Å (10 and 300 nanometer) and particle size distribution where at least 40 percent of the particles have a size lower than 300 micrometers.

* * * * *